US00PP20014P2

(12) United States Plant Patent
van der Velden

(10) Patent No.: US PP20,014 P2
(45) Date of Patent: May 19, 2009

(54) *TILLANDSIA* PLANT NAMED 'JOSEE'

(50) Latin Name: *Tillandsia cyanea*
Varietal Denomination: Josee

(75) Inventor: Josephus Maria van der Velden, Sint Oedenrode (NL)

(73) Assignee: Handelskwekerij Van Der Velden B.V., Sint Oedenrode (NL)

( * ) Notice: Subject to any disclaimer, the term of this patent is extended or adjusted under 35 U.S.C. 154(b) by 0 days.

(21) Appl. No.: 11/827,203

(22) Filed: Jul. 11, 2007

(51) Int. Cl.
*A01H 5/00* (2006.01)

(52) U.S. Cl. ..... Plt./370
(58) Field of Classification Search ..... Plt./370
See application file for complete search history.

(56) References Cited

PUBLICATIONS

UPOV–ROM GTITM, Plant Variety Database, GTI Jouve Retrieval Software, citation for *Tillandsia* plant cultivar Josee.*

* cited by examiner

*Primary Examiner*—Annette H Para

(57) ABSTRACT

A new cultivar of *Tillandsia* plant named 'Josee' that is characterized by narrow green leaves and a branched inflorescence with purple flowers.

1 Drawing Sheet

Botanical classification: *Tillandsia cyanea.*
Variety denomination: 'Josee'.

BACKGROUND OF THE INVENTION

The present invention relates to a new and distinct cultivar of *Tillandsia* plant botanically known as *Tillandsia cyanea* and hereinafter referred to by the cultivar name 'Josee'.

The new cultivar was discovered as a single plant growing in a bed of unnamed *Tillandsia cyanea* plants in 1995. The new cultivar was discovered in a cultivated area of Sint Oedenrode, The Netherlands. The exact parents are unknown.

Asexual reproduction by tissue culture of the new cultivar 'Josee' was first performed in 2003 in Sint Oedenrode, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tillandsia* cultivar 'Josee'. These traits in combination distinguish 'Josee' as a new and distinct cultivar.

1. *Tillandsia* 'Josee' exhibits narrow green leaves.
2. *Tillandsia* 'Josee' exhibits a branched inflorescence with purple flowers.

The closest comparison cultivar is *Tillandsia* 'Anita' (not patented). The new cultivar *Tillandsia* 'Josee' differs from 'Anita' by the following characteristics:

1. 'Josee' has a branched inflorescence. The inflorescence of 'Anita' is not branched.
2. 'Josee' has lighter green leaves than the leaves of 'Anita'.

BRIEF DESCRIPTION OF THE DRAWING

The accompanying photograph illustrates the distinguishing traits of *Tillandsia* 'Josee'. The plant in the photograph shows an overall view of a 4 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Tillandsia* cultivar named 'Josee'. Data was collected in Boskoop, The Netherlands from 4 year old glass greenhouse grown plants in Sint-Oedenrode, The Netherlands. The time of year was Spring. The average minimum temperature was 20° Centigrade. The light level was maintained between 17,000 and 20,000 lux. Etheral-A was applied at the rate of 1 ml. per liter of water to induce flowering.

No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Josee' has not been tested under all possible conditions and phenotypic differences may be observed with variations in environmental, climatic, and cultural conditions, however, without any variance in genotype.

Botanical classification: *Tillandsia cyanea* 'Josee'.
Parentage: The exact parents of 'Josee' are unknown.
Vigor: Moderate.
Growth rate: Moderate.
Growth habit: Broad spreading from a basal rosette.
Plant shape: Low and spreading.
Height: Average 22.1 cm. in height.
Width: Average 60.6 cm. in width.
Hardiness: USDA Zone 10.

Container size: 9 cm.
Propagation: Tissue culture.
Time to initiate roots: Approximately 70 days to produce roots by tissue culture at 25° Centigrade.
Time to produce a rooted cutting or liner in summer: Approximately 6 months to produce a rooted cutting or liner in summer at 25° Centigrade.
Time to produce a rooted cutting or liner in winter: Approximately 7 months to produce a rooted cutting or liner in winter at 25° Centigrade.
Root system: Fine and fibrous.
Foliage:
*Texture.*—Smooth, moderately glossy.
*Leaf arrangement.*—Rosulate, placed in a basal rosette.
*Quantity of leaves per plant.*—46.
*Leaf shape.*—Linear, arching downward.
*Leaf apex.*—Long acute.
*Leaf base.*—Sheathing.
*Leaf length.*—Average 31.2 cm. in length.
*Leaf width.*—Average 1.1 cm. in width.
*Pubescence.*—Absent.
*Leaf margin.*—Entire.
*Vein pattern.*—Parallel.
*Young leaf color* (*upper surface*).—Between 137B and 146A, base striped 177A.
*Young leaf color* (*lower surface*).—146A, base 166A.
*Mature leaf color* (*upper surface*).—146A, base striped 177A.
*Mature leaf color* (*lower surface*).—146A, base 166A.
*Vein color* (*lower surface*).—146A.
*Vein color* (*upper surface*).—146A.
*Durability of foliage to stress.*—High.
Flower:
*Flowering arrangement.*—Terminal compound cincinnus.
*Inflorescence type.*—Branched cincinnus.
*Inflorescence dimensions.*—Average width 5.9 mm. and 12.9 cm. in height.
*Flowering habit.*—Continuous.
*Flower form.*—Single.
*Quantity of flowers per inflorescence.*—Average of main cincinnus 17, average of secondary cincinna 9.
*Quantity of flower stems per plant.*—Average 3.
*Quantity of flowers and buds per plant.*—Average 59, one main cincinnus and an average of 5 secondary cincinna.
*Flowering season.*—Winter.
*Rate of flower opening.*—5% of the flowers are open at any stage.
*Fragrance.*—Moderately faint, sweet, and pleasant.
*Self-cleaning or persistent.*—Persistent.
*Flower bud length.*—3.5 cm. in length.
*Flower bud diameter.*—4.0 mm. in diameter.
*Flower bud shape.*—Linear, bud enclosed by a colorful bract.
*Bud color.*—198A, apex 64A; base 157A.
*Rate of bud opening.*—4 days.
*Flower aspect.*—Upward to slightly outward.
*Flower shape.*—Salverform.
*Flower width.*—5 cm.
*Flower height.*—6.1 cm.
*Flower longevity.*—Over 14 days.
*Petal appearance.*—Glossy, dull.
*Petal texture.*—Glabrous.
*Petal arrangement.*—Rotate.
*Number of petals.*—Three in number.
*Petals fused or unfused.*—Unfused.
*Petal shape.*—Spathulate.
*Petal margin.*—Entire.
*Petal apex.*—Broad acute.
*Petal dimensions.*—8 cm. in length and 2.3 cm. in width.
*Petal color when opening* (*upper side*).—N88A, base N81A; lower half of the petal 155C.
*Petal color when opening* (*under side*).—N88B, base N88A; lower half of the petal 155C.
*Petal color when fully opened* (*upper side*).—N88A, base N81A; lower half of the petal 155C.
*Petal color when fully opened* (*under side*).—N88B, base N88A; lower half of the petal 155C.
*Petal color fading to.*—N88A.
Sepals:
*Sepal appearance.*—Glossy and smooth.
*Sepal arrangement.*—Paired, placed at both sides of the corolla.
*Number of sepals.*—Two in number.
*Sepal shape.*—Narrow lanceolate, strong involute.
*Sepal margin.*—Entire.
*Sepal tip.*—Long acute.
*Sepal base.*—Cuneate.
*Sepal length.*—Average 3.7 cm.
*Sepal width.*—Average 3.5 cm.
*Sepal color, immature, upper surface.*—145D, margins 145B; apex flushed 63C.
*Sepal color, immature, under surface.*—145D, margins 145B; apex flushed 63C.
*Sepal color, mature, upper surface.*—145D, margins 145B; apex flushed 63C.
*Sepal color, mature, under surface.*—145D, margins 145B; apex flushed 63C.
Calyx:
*Calyx shape.*—Tubular.
*Calyx length.*—Average 6.1 cm in length.
*Calyx width.*—Average 5.0 mm in diameter.
Peduncle:
*Peduncle dimensions.*—Average 5.2 cm. in length and 4 mm. in diameter.
*Peduncle angle.*—0° from vertical.
*Peduncle color.*—146C, flushed 187B.
*Peduncle strength.*—Strong.
Bracts:
*Bract quantity.*—1.
*Bract shape.*—Lanceolate.
*Bract dimensions.*—Average 4.6 cm in length, 8 mm in width and 1.3 cm in length.
*Bract tip.*—Acute.
*Bract margin.*—Entire.
*Bract base.*—Sheathing.
*Bract color upper side.*—145C with margin 71C.
*Bract color under side.*—67A with 145A toward the base.
Reproduction organs:
*Stamen quantity.*—Average 6.
*Anther shape.*—Linear.
*Anther size.*—5 mm.
*Anther filament size.*—2.2 cm.
*Anther color.*—7A, filament 155C.
*Amount of pollen.*—High.
*Pollen color.*—7A to 9A.
*Pistil number.*—One in number.
*Pistil length.*—Average 8 mm.
*Stigma shape.*—Club-shaped, three-lobed.

*Stigma color.*—150D.
*Style length.*—4 mm.
*Style color.*—155C.
*Ovary color.*—155C.

Seed: Seed production has not been observed.

Disease resistance: Plants of the new *Tillandsia* are resistant to root diseases.

Pest resistance: Plants of the new *Tillandsia* have not been observed for pest resistance.

It is claimed:

1. A new and distinct variety of *Tillandsia* plant named 'Josee' as described and illustrated.

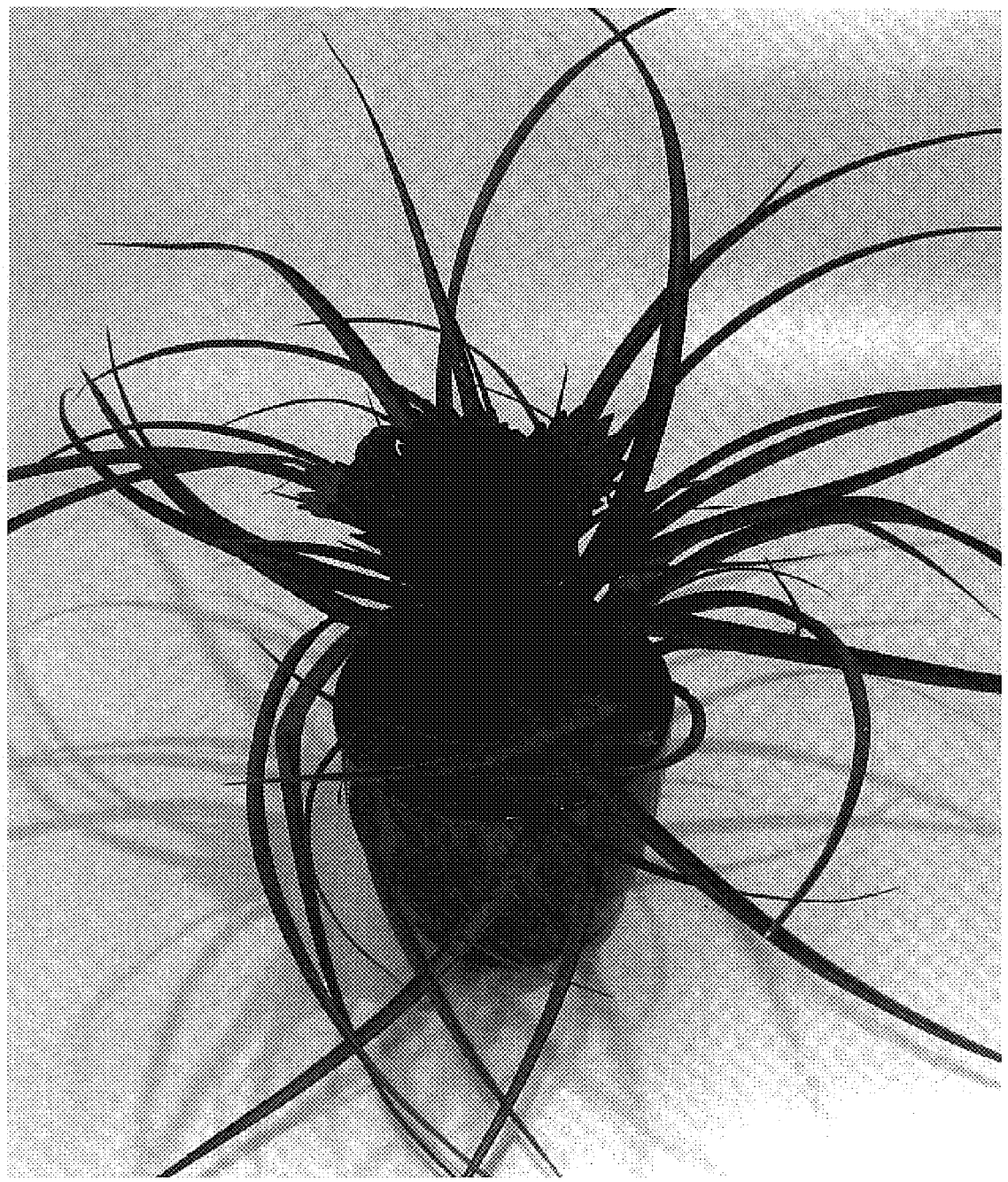

* * * * *